United States Patent

Banholzer et al.

[11] 4,042,700
[45] Aug. 16, 1977

[54] QUATERNARY N-β-SUBSTITUTED N-ALKYL-NORTROPINE BENZILATES

[75] Inventors: Rolf Banholzer, Ingelheim am Rhein; Rudolf Bauer, Wiesbaden; Alex Heusner, Gau-Algesheim; Werner Schulz, Ingelheim, am Rhein, all of Germany

[73] Assignee: Boehringer Ingelheim GmbH, Ingelheim am Rhein, Germany

[21] Appl. No.: 720,245

[22] Filed: Sept. 3, 1976

[30] Foreign Application Priority Data

Sept. 12, 1975 Germany ............................ 2540633

[51] Int. Cl.² ...................... A61K 31/46; C07D 471/08
[52] U.S. Cl. ..................................... 424/265; 260/292
[58] Field of Search ......................... 260/292; 424/265

[56] References Cited

U.S. PATENT DOCUMENTS 3,505,337  4/1970  Zeile et al. ............................ 260/292

OTHER PUBLICATIONS

Molina et al., Chem. Abstracts, vol. 63(5), 6209—d, Aug. 30, 1965.

*Primary Examiner*—Alan L. Rotman
*Attorney, Agent, or Firm*—Hammond & Littell; von Ehrlich, Chem. Abstracts, vol. 67(8), 43988d, Aug. 21, 1967.

[57] ABSTRACT

Compounds of the formula

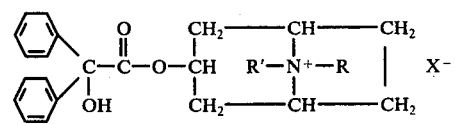

wherein
 one of R and R' is alkyl of 1 to 4 carbon atoms,
 the other of R and R' is β-haloethyl or β-hydroxyethyl, and
 X is a pharmacologically acceptable anion, preferably halogen;

the compounds as well as the salts are useful as spasmolytics, bronchospasmolytics and inhibitors of excessive stomach juice secretion.

11 Claims, No Drawings

QUATERNARY N-β-SUBSTITUTED N-ALKYL-NORTROPINE BENZILATES

This invention relates to novel N-β-substituted N-alkyl-nortropine benzilates and non-toxic acid addition salts thereof, as well as to a method of preparing those compounds.

More particularly, the present invention relates to a novel class of quaternary N-β-substituted N-alkyl-nortropine benzilates represented by the formula

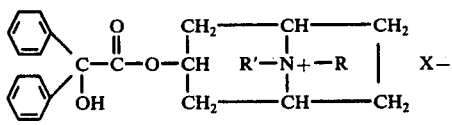

(I)

wherein
one of R and R' is alkyl of 1 to 4 carbon atoms,
the other of R and R' is β-haloethyl or β-hydroxyethyl, and
X is a pharmacologically acceptable anion, preferably halogen.

The compounds embraced by formula I may be prepared by reacting a compound of the formula

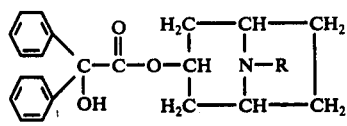

(II)

with a compound of the formula

R' — Y (III)

where R and R' have the meanings defined in connection with formula I, and Y is a reactive group which can be split off as an anion, such as halogen, toluenesulfonyl or methanesulfonyl, and, if required, converting the reaction product into a salt with a pharmacologically acceptable anion.

A compound of the formula I wherein R' is β-haloethyl may also be prepared by halogenating a corresponding compound where R' is β-hydroxy-ethyl.

The quaternization reaction may be carried out in an inert organic solvent, such as acetonitrile, toluene, chloroform or acetone, and the operative temperature range lies between 0° C and the boiling point of the reaction mixture.

The intermediate tertiary compounds of the formula II, which are also new, may be prepared by reacting nortropine benzilate with an alkylating agent of the formula

R — Y (IV)

where R and Y have the meanings previously defined, under the conditions indicated above for the quaternization reaction. In this case as well, the β-haloethyl-substituted compounds can be prepared from the corresponding β-hydroxyethyl-substituted compounds. The tertiary intermediates may, if desired, be converted in conventional manner into their acid addition salts.

The starting compound, nortropine benzilate, is a known compound and may be obtained by the method of Pfleger et al., Arzneimittelforschung 17,719 (1967).

The following examples illustrate the present invention and will enable others skilled in the art to understand it more completely. It should be understood, however, that the invention is not limited solely to the particular examples given below.

EXAMPEL 1

N-β-fluoroethyl-nortropine benzilate hydrochloride

A mixture consisting of 146.0 gm (0.434 mol) of nortropine benzilate, 60.6 gm (0.477 mol) of 2-bromo-fluoroethane, 101.1 gm (0.954 mol) of sodium carbonate and 1200 ml of acetonitrile was refluxed for 10 hours while stirring. Thereafter, the acetonitrile was distilled off, the residue was taken up in a mixture of water and methylene chloride, and the alkaline aqueous phase was extracted repeatedly with methylene chloride. The combined methylene chloride phases were dried over sodium sulfate, the sodium sulfate was suction-filtered off, and N-β-fluoroethyl-nortropine benzilate hydrochloride was precipitated from the filtrate with hydrogen chloride. Yield: 131.3 gm (91.2% of theory). White crystals (from methanol/ether), m.p. 209° C (decomp.). Elemental and spectrum analysis confirmed the identity of this compound.

EXAMPLE 2

N-β-fluoroethyl-nortropine benzilate methobromide 109.9 gm (0.287 mol) of N-β-fluoroethyl-nortropine benzilate (liberated from its hydrochloride in the conventional way) were dissolved in a solvent mixture consisting of 450 ml of absolute methylene chloride and 300 ml of absolute acetonitrile, and quaternized with 136.1 gm (1,433 mol) of methyl bromide at room temperature. After 3 days the crystallizate was suction-filtered off, washed with acetone and dried at 50° C in a vacuum of 12 mm Hg. Yield: 129.8 gm (94.7% of theory). White crystals (from acetonitrile), m.p. 192°–193° C (decomp.). Elemental and spectrum analysis confirmed the identity of this compound.

EXAMPLE 3

N-β-fluoroethyl-nortropine benzilate ethobromide 10.2 gm (0.0266 mol) of N-β-fluoroethyl nortropine benzilate (liberated from its hydrochloride in the conventional way) were refluxed in 30 ml of absolute acetonitrile while gradually adding a total of 23.2 gm (0.213 mol) of ethyl bromide. As the reaction progressed, white crystals gradually precipitated from the reaction solution. After 14 days the precipitated crystals were collected by suction filtration, washed with methylene chloride and dried at 50° C in a vacuum of 12 mm Hg. Yield: 9.2 mg (70.2% of theroy). White crystals (from acetonitrile/ether), m.p. 215° to 216° C (decomp.). Elemental and spectrum analysis confirmed the identity of this compound.

EXAMPLE 4

N-β-fluoroethyl-nortropine benzilate butobromide 6.7 gm (0.0175 mol) of N-β-fluoroethyl-nortropine benzilate (liberated from its hydrochloride in the usual way) were refluxed in 20 ml of absolute acetonitrile with 12.0 gm (0.0875 mol) of n-butyl bromide. The reaction was allowed to proceed for 3 weeks, during which period another 12.0 gm of n-butyl bromide were added to the reaction mixture. After the reaction had gone to completion the solvent was distilled off, and the residue was recrystallized from acetonitrile/ether. Yield: 1.2 gm (25.3% of theory). White crystals (from acetonitrile/ether), m.p. 201°-202° C (decomp.). Elemental and spectrum analysis confirmed the identity of this compound.

EXAMPLE 5

Tropine benzilate β-fluoro-ethobromide 7.0 gm (0.02 mol) of tropine benzilate and 2.8 gm (0.022 mol) of 2-fluoroethyl bromide were refluxed in 50 ml of absolute acetonitrile. As the reaction proceeded, crystals precipitated from the reaction solution. The reaction was allowed to proceed for 1 week, during which period another 2.8 gm (0.22 mol) of 2-fluoroethyl bromide were added. After the reaction had gone to completion, the crystals were collected by suction filtration and washed with methylene chloride. Yield: 8.1 gm (85% of theory). White crystals (from methanol/ether), m.p. 242°-243° C (decomp.). Elemental and spectrum analysis confirmed the identity of this compound.

EXAMPLE 6

N-ethyl-nortropine benzilate β-fluoro-ethobromide 7.3 gm (0.02 mol) of N-ethyl-nortropine benzilate [a known compound described in the literature, which may be prepared analogous to Example 3 or 8 from nortropine benzilate and ethyl bromide; N-ethyl-nortropine-benzilate hydrochloride, m.p. 228° C (decomp.), white crystals from acetonitrile] and 2.8 gm (0.022 mol) of 2-fluoroethyl bromide were refluxed in 50 ml of absolute acetonitrile. Crystals precipitated from the reaction solution as the reaction proceeded. The reaction was allowed to proceed for 2½ weeks, during which period another 5.6 gm (0.044 mol) of 2- fluoroethyl bromide were added. The crystals were then collected by suction filtration, washed with methylene chloride and dried at 50° C in a vacuum of 12 mm Hg. Yield: 6.7 gm (68.1% of theory). White crystals (from ethanol), m.p. 238°-239° C (decomp.). Elemental and spectrum analysis confirmed the identity of this compound.

EXAMPLE 7

N-n-butyl nortropine benzilate β-fluoroethyl bromide 7.9 gm (0.02 mol) of N-n-butyl-nortropine benzilate [a known compound described in the literature, which may be prepared analogous to Example 3 or 8 from nortropine benzilate and n-butyl bromide; N-n-butyl-nortropine benzilate, m.p. 105° to 106° C, white crystals from acetonitrile] and 2.8 gm (0.022 mol) of 2-fluoroethyl bromide were refluxed in 50 ml of absolute acetonitrile. The reaction was allowed to proceed for 2 weeks, during which period another 5.6 gm (0.044 mol) of 2-fluoroethyl bromide were added.

After the reaction had gone to completion, the solvent was distilled off, and the residue was admixed with acetone. The crystallizate formed thereby was collected, washed with acetone and dried at 50° C in a vacuum of 12 mm Hg. Yield: 7.3 gm (69.9% of theory). White crystals (from ethanol), m.p. 214°-215° C (decomp.). Elemental and spectrum analysis confirmed the identity of this compound.

EXAMPLE 8

N-β-hydroxyethyl-nortropine benzilate hydrochloride 44.9 gm (0.12 mol) of nortropine benzilate hydrochloride, 15.0 gm (0.12 mol) of bromoethanol and 25.4 gm (0.24 mol) of sodium carbonate were refluxed in 200 ml of acetonitrile while stirring. After a reaction period of 4 hours, another 7.5 gm (0.06 mol) of bromoethanol were added.

After a total reaction period of 6 hours the solvent was distilled off, the residue was taken up in a mixture of water and methylene chloride, and the alkaline aqueous phase was separated and extracted repeatedly with methylene chloride.

The combined methylene chloride phases were dried over sodium sulfate, the sodium sulfate was separated by suction filtration, and the solvent was distilled out of the filtrate.

The distillation residue, i.e. the hydrobromide, crystallized and was used without purification.

The yield was almost quantitative. White crystals (from acetonitrile), m.p. 121°-122° C. The hydrochloride was prepared from the hydrobromide in the conventional way: White crystals (from methanol/ether), m.p. 203° C (decomp.). Elemental and spectrum analysis confirmed the identity of this compound.

EXAMPLE 9

N-β-chloroethyl-nortropine benzilate hydrochloride 11.0 gm (0.026 mol) of N-β-hydroxyethyl-nortropine benzilate hydrochloride were refluxed in 50 ml of thionyl chloride for 1 hour. Then the thionyl chloride was distilled off under reduced pressure, and the distillation residue was admixed for hydrolysis with 30 ml of water. After standing at room temperature overnight, the water was distilled off in a water aspirator vacuum, and the distillation residue, which should not show any acid reaction any more, was recrystallized from acetone/ether and dried at 50° C in a vacuum of 12 mm Hg. Yield: 9.5 gm (82.7% of theory) of hydrochloride. White crystals (from ethanol/ether), m.p. 227° C (decomp.).

EXAMPLE 10

N-β-chloroethylnortropine-benzilate methobromide 1.6 gm (0.004 mol) of N-β-chloroethyl-nortropine benzilate (liberated from its hydrochloride in the usual way) were quaternized in a solution of 10 ml of absolute acetonitrile with 1.9 gm (0.02 mol) of methyl bromide at room temperature.

After 3 days the crystallizate was collected by suction filtration, washed with a little acetone and dried at 50° C in a vacuum of 12 mm Hg. Yield: 1.8 gm (90.9% of theory). White crystals (from acetonitrile), m.p. 194°-195° C (decomp.). Elemental and spectrum analysis confirmed the identity of this compound.

EXAMPLE 11

N-β-hydroxyethyl-nortropine benzilate methobromide 5.0 gm (0.013 mol) of N-β-hydroxyethyl-nortropine benzilate were quaternized in 20 ml of absolute methylene chloride and 15 ml of absolute acetonitrile with 6.2 gm (0.065 mol) of methyl bromide at room temperature. The reaction was allowed to proceed for 4 days during which another 6.2 gm (0.065 mol) of methyl bromide dissolved in acetonitrile were added. Then the crystallizate which had formed was collected by suction filtration, washed with a little acetone and dried at 50° C in a vacuum of 12 mm Hg. Yield: 5.0 gm (80.1% of theory). White crystals (from methanol/ether), m.p. 221°-222° C (decomp.). Elemental and spectrum analysis confirmed the identity of this compound.

EXAMPLE 12

N-β-hydroxyethyl-nortropine benzilate ethobromide 10.0 gm (0.0262 mol) of N-β-hydroxyethyl-nortropine benzilate were refluxed in 30 ml of absolute acetonitrile with 5.7 gm (0.0524 mol) of ethylbromide. Crystals precipitated from the solution as the reaction progressed. After 3 days the precipitated crystals were collected by suction filtration, washed with methylene chloride and dried at 50° C in a vacuum of 12 mm Hg. Yield: 6.1 mg (47.4% of theory). White crystals (from acetonitrile), m.p. 212°-213° C (decomp.). Elemental and spectrum analysis confirmed the identity of this compound.

EXAMPLE 13

N-β-chloroethyl-nortropine benzilate ethobromide 2.0 gm (0.0041 mol) of N-β-hydroxyethyl-nortropine benzilate ethobromide were refluxed in 10 ml of thionyl chloride for 15 minutes. Afterwards the thionyl chloride was distilled off under reduced pressure, and the distillation residue was admixed with 50 ml of water for hydrolysis. After standing overnight, the acid solution was extracted with methylene chloride, and the separated aqueous phase was saturated with sodium chloride, whereupon crystallization took place gradually. The crystals were collected by suction filtration and dried at 50° C in a vacuum of 12 mm Hg. Yield: 0.5 gm (24.1% of theory). White crystals (from acetonitrile), m.p. 205°-204° C (decomp.). Elemental and spectrum analysis confirmed the identity of this compound.

EXAMPLE 14

N-β-hydroxyethyl-nortropine benzilate n-butobromide 9.5 gm (0.0249 mol) of β-hydroxyethyl-nortropine benzilate were refluxed in 25 ml of absolute acetonitrile with 34.1 gm (0.249 mol) of n-butyl bromide. The reaction was allowed to proceed for 10 days, whereupon the solvent was distilled off under reduced pressure, the distillation residue was dissolved in methylene chloride, and the resulting solution was extracted with water which had been made alkaline with sodium carbonate.

The acqueous phases, neutralized with hydrobromic acid, were freeze-dried, and the resulting product was recrystallized from isopropanol. Yield: 3.0 gm (23.2% of theory). White crystals (from isopropanol), m.p. 102°-103° C (decomp. with cristallic alcohol). Elemental and spectrum analysis confirmed the identity of this compound.

EXAMPLE 15

N-β-chloroethyl-nortropine benzilate n-butobromide 4.8 gm (0.0093 mol) of N-β-hydroxyethyl-nortropine benzilate n-butobromide were refluxed in 30 ml of thionyl chloride for 30 minutes. Thereafter, the thionyl chloride was distilled off under reduced pressure, and the residue was taken up in a mixture of 100 ml of water and 20 ml of acetone. For hydrolysis, the resulting solution was allowed to stand at room temperature for 24 hours. By means of sodium carbonate the pH-value was adjusted to between 4 and 5, and the acetone was distilled off under reduced pressure.

Thereupon the aqueous solution was extracted several times with methylene chloride, the combined methylene chloride phases were dried over sodium sulfate, and the methylene chloride was distilled off. The distillation residue crystallized upon trituration with acetone. The crystals were collected by suction filtration, washed with a little acetone and dried at 50° C in a vacuum of 12 mm Hg. Yield: 3.1 gm (62.4% of theory). White crystals (from isopropanol), m.p. 205° C (decomp.). Elemental and spectrum analysis confirmed the identity of this compound.

EXAMPLE 16

Tropine benzilate β-hydroxyethobromide 12.0 gm (0.0341 mol) of tropine benzilate were refluxed in 100 ml of absolute acetonitrile with 8.5 gm (0.068 mol) of bromoethanol. White crystals precipitated gradually from the solution as the reaction progressed. After 6½ hours the precipitated crystals were collected by suction filtration, washed with acetonitrile and dried at 50° C in a vacuum of 12 mm Hg. Yield: 15.6 gm (95.9% of theory). White crystals (from methanol), m.p. 256°-257° C (decomp.). Elemental and spectrum analysis confirmed the identity of this compound.

EXAMPLE 17

Tropine benzilate β-chloroethobromide 9.5 gm (0.0193 mol) of tropine benzilate β-hydroxyethobromide were refluxed in 70 ml of thionyl chloride for 30 minutes.

Then the thionyl chloride was distilled off under reduced pressure, and the distillation residue was admixed with 80 ml of water for hydrolysis.

After standing for 3½ hours at room temperature and subsequent clarification with activated charcoal, the acid solution was adjusted to a pH-value of 5 to 6 with sodium carbonate and then freeze-dried.

The residue was extracted with absolute ethanol for removal of sodium chloride. By oven-saturation with ether, crystallization was initiated.

The crystals were collected by suction filtration, washed with a mixture of ethanol and ether and dried at 50° C in a vacuum of 12 mm Hg. Yield: 7.8 gm (79.0% of theory). White crystals (from ethanol/ether), m.p. ~100° C (with cristallic alcohol.

By boiling with methylene chloride the melting point was raised to 154°-155° C. Elemental and spectrum analysis confirmed the identity of this compound.

EXAMPLE 18

N-ethyl-nortropine benzilate β-hydroxyethobromide 9.0 gm (0.0246 mol) of N-ethyl-nortropine benzilate (a known compound which is described in the literature and may be prepared analogous to Example 3 or 8) were refluxed in 50 ml of absolute acetonitrile with 6.2 gm (0.0496 mol) of bromoethanol.

After a 4-day reaction period the solvent was distilled off and the distillation residue was boiled with acetone. The crystals formed thereby were collected by suction filtration, washed with a little acetone and dried at 50° C in a vacuum of 12 mm Hg. Yield: 6.2 gm (51.3% of theory). White crystals (from ethanol), m.p. 216°-217° C (decomp.). Elemental and spectrum analysis confirmed the identity of this compound.

EXAMPLE 19

N-ethyl-nortropine benzilate β-chloroethobromide 4.9 gm (0.01 mol) of N-ethyl-nortropine benzilate β-hydroxyethobromide were refluxed in 30 ml of thionyl chloride for 30 minutes.

Thereafter, the thionyl chloride was distilled off under reduced pressure and the distillation residue was admixed for hydrolysis with a solvent mixture consisting of 100 ml of water and 20 ml of acetone. After standing overnight, the mixture was adjusted with sodium carbonate to a pH-value of 4 to 5, the acetone was distilled off under reduced pressure, and the residual turbid solution was saturated with sodium chloride, whereupon crystals separated out.

The crystals were collected by suction filtration and dried at 50° C in a vacuum of 12 mm Hg. Yield: 4.6 gm (90.6% of theory). White crystals (from methanol/ether), m.p. 214°–215° C (decomp.). Elemental and spectrum analysis confirmed the identity of this compound.

EXAMPLE 20

N-n-butyl-nortropine benzilate β-hydroxyethobromide 15.7 gm (0.0399 mol) of N-n-butyl-nortropine benzilate (see Example 7) were refluxed in 80 ml of absolute acetonitrile with 10.0 gm (0.04 mol) of bromoethanol.

After a 5-day reaction period the solvent was distilled off, and the distillation residue was boiled with acetone. The crystals formed thereby were collected by suction filtration, washed with a little acetone and dried in a vacuum of 12 mm Hg at 50° C. Yield: 12.5 gm (60.4% of theory. White crystals (from ethanol), m.p. 223°–224° C (decomp.). Elemental and spectrum analysis confirmed the identity of this compound.

EXAMPLE 21

N-n-butyl-nortropine benzilate β-chloroethobromide 4.0 gm (0.077) mol of N-n-butyl-nortropine benzilate β-hydroxyethobromide were refluxed in 20 ml of thionyl chloride for 35 minutes.

Afterwards, the thionyl chloride was distilled off under reduced pressure, and the distillation residue was admixed with a solvent mixture consisting of 100 ml of water and 30 ml of acetone. After standing for 24 hours and then adjusting the pH-value to 4–5 with sodium carbonate, the acetone was distilled off under reduced pressure, and the residual aqueous solution was extracted with ether and then saturated with sodium chloride, whereupon crystals separated out. The crystals were collected by suction filtration and dried at 50° C in a vacuum of 12 mm Hg. Yield: 4.0 gm (96.6% of theory). White crystals (from ethanol/ether), m.p. 217° C (decomp.). Elemental and spectrum analysis confirmed the identity of this compound.

The compounds of the present invention, that is, the quaternary compounds embraced by formula I, as well as those tertiary intermediates of the formula II where R is β-hydroxy-ethyl or β-halo-ethyl and their non-toxic, pharmaceutically acceptable acid addition salts, have useful pharmacodynamic properties.

More particularly, the quaternary compounds exhibit spasmolytic and bronchospasmolytic activities as well as an inhibiting effect upon excess stomach juice secretion, and the tertiary compounds and their non-toxic acid addition salts exhibit spasmolytic activity in warm-blooded animals, such as guinea pigs, rats, mice or dogs.

Particularly preferred among the quaternary compounds of the formula I are those where R is alkyl of 1 to 4 carbon atoms, especially methyl, and R' is β-fluoro-ethyl.

Examples of non-toxic, pharmacologically acceptable acid addition salts of the tertiary compounds of the formula II are those formed with hydrochloric acid, hydrobromic acid, sulfuric acid, acetic acid, propionic acid, tartaric acid, citric acid, 8-chlorotheophylline or the like.

For pharmaceutical purposes the compounds of the present invention are administered to warm-blooded animals preferably perorally, but also parenterally, rectally or by inhalation as active ingredients in customary dosage unit compositions, that is, compositions in dosage unit form consisting essentially of an inert pharmaceutical carrier and one effective doage unit of the active ingredient, such as tablets, coated pills, capsules, wafers, powders, solutions, suspensions, emulsions, syrups, suppositories, aerosol sprays and the like. One effective oral dosage unit of the compounds according to the present invention is from 0.1 to 6.0 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 22

Tablets

The tablet composition is compounded from the following ingredients:

| | | |
|---|---:|---|
| N-β-flouroethyl-nortropine benzilate hydrochloride | 0.25 | parts |
| Lactose | 85.75 | parts |
| Potato starch | 30.0 | parts |
| Gelatin | 3.0 | parts |
| Magnesium stearate | 1.0 | parts |
| Total | 120.0 | parts |

Preparation

The active ingredient is admixed with 2.5 parts of lactose, the mixture is intensively milled, and the remainder of the lactose and the potato starch are intimately admixed therewith. The resulting mixture is moistened with an aqueous 10% solution of the gelatin and granulated through a 1.5 mm-mesh screen. The granulate is dried at 40° C, again passed through a 1 mm-mesh screen, admixed with the magnesium stearate, and the resulting composition is compressed into 120 mgm-tablets in a conventional tablet making machine. Each tablet is an oral dosage unit composition containing 0.25 mgm of the active ingredient.

EXAMPLE 23

Coated Pills

The pill core composition is compounded from the following ingredients:

| | |
|---|---:|
| N-β-fluoroethyl-nortropine benzilate methobromide | 0.25 parts |

| | | |
|---|---:|---|
| -continued | | |
| Lactose | 32.25 | parts |
| Corn starch | 15.0 | parts |
| Polyvinylpyrrolidone | 2.0 | parts |
| Magnesium stearate | 0.5 | parts |
| Total | 50.0 | parts |

Preparation

The active ingredient is admixed with 2.5 parts of lactose, the mixture is intensively milled, the remainder of the lactose and the corn starch are intimately admixed therewith, the mixture is moistened with an aqueous 15% solution of the polyvinylpyrrolidone, and the moist mass is granulated through a 1 mm-mesh screen. The granulate is dried, again passed through the screen, admixed with the magnesium stearate, and the resulting composition is compressed into 50 mgm-pill cores which are subsequently coated with a thin shell consisting essentially of a mixture of sugar and talcum and finally polished with beeswax. Each coated pill is an oral dosage unit composition containing 0.25 mgm of the active ingredient.

EXAMPLE 24

Drop Solution

The solution is compounded from the following ingredients:

| | | |
|---|---:|---|
| N-$\beta$-fluoroethyl-nortropine benzilate ethobromide | 0.0125 | parts |
| Saccharin sodium | 0.3 | parts |
| Sorbic acid | 0.1 | parts |
| Ethanol | 30.0 | parts |
| Flavoring | 1.0 | parts |
| Distilled water q.s.ad | 100.0 | parts |

Preparation

The active ingredient and the flavoring are dissolved in the ethanol (solution I). The saccharin and the sorbic acid are dissolved in the distilled water (solution II). Solution I is admixed with solution II, and the resulting composition is filtered unit free from suspended particles. 1 ml of the solution is an oral dosage unit composition containing 0.125 mgm of the active ingredient.

EXAMPLE 25

Hypodermic Solution

The solution is compounded from the following ingredients:

| | | |
|---|---:|---|
| N-$\beta$-fluoroethyl-nortropine benzilate butobromide | 0.25 | parts |
| Polyethyleneglycol | | |
| Tartaric acid | 150.0 | parts |
| Distilled water q.s.ad | 3000.0 | parts by vol. |

Preparation

The tartaric acid, the polyethyleneglycol and the active ingredient are dissolved in a sufficient amount of distilled water, the solution is diluted with additional distilled water to the indicated volume and then filtered until free from suspended matter. The filtrate is filled into 3cc-ampules in an atomsphere of nitrogen, which are then sterilized for 20 minutes at 120° C and finally sealed. The contents of each ampule comprise 0.25 mgm of the active ingredient and are an injectable dosage unit composition.

EXAMPLE 26

Suppositories

The suppository composition is compounded from the following ingredients:

| | | |
|---|---:|---|
| Tropine benzilate $\beta$-fluoro ethobromide | 0.25 | parts |
| Lactose | 4.75 | parts |
| Suppository base (e.g. cocoa butter) | 1695.0 | parts |
| Total | 1700.0 | parts |

Preparation

The active ingredient is admixed with the lactose, and the mixture is milled and then stirred with an immersion homogenized into the suppository base which had previously been melted and cooled to 40° C. The resulting composition is cooled to 37° C, and 1700 mgm-portions thereof are poured into cooled suppository molds and allowed to harden therein. Each suppository contains 0.25 mgm of the active ingredient and is a rectal dosage unit composition.

EXAMPLE 27

Aerosol

The aerosol is compounded from the following ingredients:

| | | |
|---|---:|---|
| N-$\beta$-fluoroethyl-nortropine benzilate methobromide | 0.007–0.7 | parts |
| Sorbitol trioleate (surfactant) | 0.5–2.0 | parts |
| Propellant gas mixture q.s.ad | 100 | parts |

Preparation

The ingredients are filled in conventional manner into aerosol containers equipped with a metering valve which expels 20–150$\gamma$ of the active ingredient with each actuation. The aerosol is suitable for inhalation therapy.

The amount of active ingredient and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

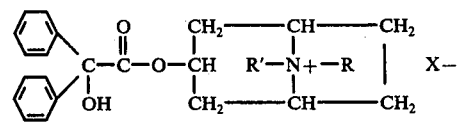

wherein
one of R and R' is alkyl of 1 to 4 carbon atoms,
the other of R and R' is $\beta$-haloethyl or $\beta$-hydroxyethyl, and
X is a pharmacologically acceptable anion.

2. A compound of claim 1, where
one of R and R' is alkyl of 1 to 4 carbon atoms,
the other of R and R' is β-haloethyl or β-hydroxyethyl, and
X is halogen.

3. A compound of claim 1, where
R is alkyl of 1 to 4 carbon atoms,
R' is β-haloethyl or β-hydroxyethyl, and
X is halogen.

4. A compound of claim 1, where
R is alkyl of 1 to 4 carbon atoms,
R' is β-fluoroethyl, and
X is halogen.

5. The compound of claim 1 which is N-β-fluoroethyl-nortropine benzilate methobromide.

6. A compound of the formula

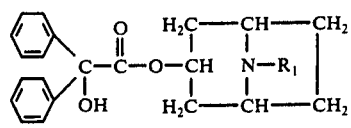

wherein $R_1$ is β-hydroxyethyl or β-haloethyl, or a non-toxic, pharmacologically acceptable acid addition salt thereof.

7. A compound of claim 1, which is N-β-fluoroethyl-nortropine benzilate or a non-toxic, pharmacologically acceptable acid addition salt thereof.

8. A spasmolytic or bronchospasmolytic pharmaceutical dosage unit composition consisting essentially of an inert pharmaceutical carrier and an effective spasmolytic or bronchospasmolytic amount of a compound of claim 1.

9. A spasmolytic pharmaceutical dosage unit composition consisting essentially of an inert pharmaceutical carrier and an effective spasmolytic amount of a compound of claim 6.

10. The method of alleviating spasms or bronchospasms in a warm-blooded animal, which comprises administering to said animal an effective spasmolytic or bronchospasmolytic amount of a compound of claim 1.

11. The method of alleviating spasms in a warm-blooded animal, which comprises administering to said animal an effective spasmolytic amount of a compound of claim 6.

* * * * *